United States Patent [19]

Kinghorn et al.

[11] Patent Number: 4,468,328
[45] Date of Patent: Aug. 28, 1984

[54] PURIFICATION OF 12-O-TETRADECANOYLPHORBOL-13-ACETATE, PHORBOL, AND 4α-PHORBOL FROM CROTON OIL

[75] Inventors: Alan D. Kinghorn; Gary T. Marshall, both of Chicago, Ill.

[73] Assignee: The Board of Trustees of the University of Ill., Urbana, Ill.

[21] Appl. No.: 435,070

[22] Filed: Jan. 17, 1983

[51] Int. Cl.$^3$ ............................................ B01D 15/08
[52] U.S. Cl. ................................. 210/634; 210/656; 210/658
[58] Field of Search ...................... 210/658, 656, 198.3, 210/634; 422/70; 562/598, 600; 426/430

[56] References Cited

U.S. PATENT DOCUMENTS 3,962,074  6/1976  Schrom ............................. 210/634
3,996,132 12/1976  Mateos ............................. 210/634

OTHER PUBLICATIONS

Thin-Layer Chromatography An Annotated Bibliography: 1964–1968 by Haywood. Ann Arbor Science Pub. Ann Arbor, Mich. p. 261, 1968.
Isolation of Phorbal and 4α-Phorbol from Croton Oil by Marshall and Kinghorn in Journal of Chromatography 206(1981)421–424.

Primary Examiner—John Adee
Attorney, Agent, or Firm—Mathew L. Kalinoski

[57] ABSTRACT

Droplet counter-current chromatography is utilized to isolate and purify 12-O-tetradecanoylphorbol-13-acetate (TPA), phorbol, and the diastereoisomer 4α-phorbol from croton oil. The stationary and mobile phases for the procedure are derived from an equilibrated mixture of hexane-diethylether-n-propanol-ethanol-water, the separated upper layer of which comprises the stationary phase and the bottom layer of which the mobile phase. The TPA and the phorbol isomers are obtained in exceptionally high purity by further treatment with liquid column chromatography and thin-layer chromatography.

9 Claims, No Drawings

PURIFICATION OF 12-O-TETRADECANOYLPHORBOL-13-ACETATE, PHORBOL, AND 4α-PHORBOL FROM CROTON OIL

This invention relates to a method for isolating phorbol esters, phorbol, and the diastereoisomer 4α-phorbol from croton oil. More particularly, this invention relates to a method combining droplet countercurrent chromatography (DCCC), liquid column chromatography, and thin-layer chromatography as a means for isolating 12-0-tetradecanoylphorbol-13-acetate (TPA), phorbol, and 4α-phorbol in exceptionally high purity from croton oil.

TPA and its phorbol ester analogs are of considerable importance in cancer research because of their activity as tumor-promoting agents or cocarcinogens for mouse skin, with TPA being the most potent representative of this series. The isomeric diterpene alcohols, namely phorbol and 4α-phorbol, produced by hydrolysis of the phorbol esters, are useful for the semisynthesis of various esters that are employed in structure-activity studies. Esters of 4α-phorbol are non-cocarcinogenic and are useful as negative controls.

In early work, eleven active tumor promoters were resolved from croton oil and were shown to be various esters of the diterpene alcohol phorbol[Hecker, E., Methods Cancer Res. 6, 439 (1971)]. Later, Hecker et al. showed TPA to be the most potent tumor promoter, and using semisynthetic phorbol esters, defined a range of structure-activity relationships in the mouse, assayed both by tumor promoting activity and by inflammatory activity on the mouse ear [Hecker, E. et al., Prog. Chem. Org. Nat. Prod. 31, 377 (1974)].

TPA, phorbol, 4α-phorbol, and several commonly used phorbol and 4α-phorbol esters for cancer research studies are depicted as follows:

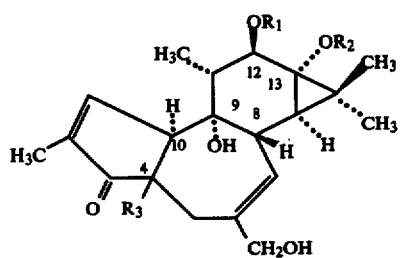

TPA  ($R_1$=—CO(CH$_2$)$_{12}$CH$_3$; $R_2$=—COCH$_3$; $R_3$=β—OH)
PHORBOL ($R_1$=$R_2$=—H; $R_3$=β—OH) 4α-PHORBOL ($R_1$=$R_2$=—H; $R_3$=α—OH)
PHORBOL 12,13-DIDECANOATE ($R_1$=$R_2$=—CO(CH$_2$)$_8$CH$_3$; $R_3$=β—OH)
4α-PHORBOL 12,13-DIDECANOATE ($R_1$=$R_2$=—CO(CH$_2$)$_8$CH$_3$; $R_3$=α—OH)
PHORBOL 12,13-DIBENZOATE ($R_1$=$R_2$=—COC$_6$H$_5$; $R_3$=β—OH)
PHORBOL 12,13-DIACETATE ($R_1$=$R_2$=—COCH$_3$; $R_3$=β—OH)

4α-Phorbol 12,13-didecanoate, the epimer of phorbol 12,13-didecanoate, is known to be inactive on mouse skin as an inflammatory and tumor-producing agent and is accordingly useful as an important negative control material in vivo and in vitro.

Prior-art methods for the isolation of phorbol and phorbol esters from croton oil are tedious and lengthy in that they involve extensive use of the cumbersome and expensive Craig counter-current distribution apparatus (Hecker, E. et al. loc. cit.).

Accordingly, it is an object of this invention to provide a novel, simple, and inexpensive method for the isolation of TPA and the phorbol isomers in high purity.

It is another object of this invention to provide a droplet counter-current chromatographic procedure for the isolation of TPA and phorbol isomers.

It is still another object of this invention to provide a combined DCCC, liquid column chromatography, and thin-layer chromatography procedure for the isolation of TPA and phorbol isomers in exceptionally high purity.

These and other objects will become apparent as description of the invention proceeds.

In accordance with this invention, TPA and the phorbol esters are isolated from croton oil in a DCCC procedure utilizing a solvent system derived from an equilibrated mixture of hexane-diethylether-n-propanol-ethanol-water. The separated upper layer of the equilibrated mixture comprises the stationary phase and the bottom layer the mobile phase in the DCCC procedure. The composition of the solvent system is such that droplets of suitable size and mobility are generated and that efficient and rapid partitioning is effected of the TPA and the phorbol isomers between the stationary and mobile phases. To this end, the distribution coefficient for TPA and the phorbol isomers, as defined by the ratio of their concentrations in the stationary phase divided by that in the mobile, phase should lie in the range of about 3.0 to about 12.0, preferable in the range of about 5.0 to about 8.0. A composition that can be used to advantage comprises hexane-diethylether-n-propanol-ethanol-water in volume proportions of about 1:2:1:1:1.

For the isolation and purification of TPA, croton oil is extracted first with an aqueous alcohol solution. Suitably, a hexane solution of croton oil is extracted with aqueous methanol to yield a crude TPA extract. The extract is dissolved in a small amount of the above-described partitioning solvent and is fed to a DCCC apparatus (Model-A DCCC, Tokyo Rikaikikai, Tokyo, Japan). The TPA-rich fractions are collected, combined and further purified by liquid column chromatography. The procedure can suitable by performed on a LiChoprep RP-8 (40–60 μm) Size A column using octylsilyl phase-bonded silica gel and mixtures of water-acetonitrile-methanol of decreasing polarity as the eluting solvent. The TPA-rich fractions are again collected, combined and subjected to final purification by preparative thin layer chromatography using silica gel G layers and chloroform-ethyl acetate as the solvent. The bands rich in TPA are scraped from the plates, combined and eluted with diethylether-methanol to yield TPA of exceptionally high purity.

For the isolation of the phorbol isomers, the croton oil from which crude TPA has been extracted is treated with a base under an inert atmosphere to hydrolyze the residual phorbol esters. Suitable conditions, by way of example, are treatment of the croton oil with methanol saturated with Ba(OH)$_2$.8H$_2$O under an atmosphere of nitrogen. The crude phorbol isomers produced are solvent extracted from the croton oil and submitted to DCCC separation in the apparatus and with the solvent system described above for the separation of TPA. The phorbol-rich fractions are combined and the isomers are further purified and separated by liquid column chromatography with the column and solvent system described for the purification of TPA. Phorbol is eluted first and then 4α-phorbol, both isomers in exceptionally high purity.

DESCRIPTION OF THE PREFERRED EMBODIMENTS

The invention is further illustrated by reference to the following examples and procedures.

Apparatus. DCCC separations were carried out on a Model-A DCCC apparatus (Tokyo Rikaikikai, Tokyo, Japan). Low pressure liquid column chromatography was performed on a LiChoprep RP-8 (40–60μm), Size A column (Merck, Darmstadt, G. F. R.). Preparative and thin layer chromatography were performed on silica gel G layers (20×20 cm plates, 250 μm) Merck, Darmstadt, G. F. R.).

Materials. Croton oil and reference TPA were obtained from Sigma Chemical Company, St. Louis, Missouri. Reagent grade solvents were used throughout and were distilled in glass before use.

EXAMPLE 1

Solvent fractionation. Croton oil (100 g) was dissolved in 100 ml hexane, and this solution was extracted with 4×50 ml aliquots of methanol-water (20:3). The aqueous phase was found to contain the bulk of the TPA and was concentrated to dryness under reduced pressure at 40° C., to yield 3.35 g of a residue.

Droplet counter-current chromatography (DCCC). The solvent system for DCCC comprised hexane-diethylether-n-propanol-ethanol-water (340 ml, 800 ml, 300 ml, 500 ml, and 400 ml, respectively). After equilibration for 4 hr in a 4 liter separatory funnel, the lower phase was removed and pumped into the DCCC apparatus, to serve as the stationary phase for the DCCC operation. A portion (455 mg) of the TPA-containing residue from the solvent fractionation step was dissolved in 10 ml of the DCCC mobile and stationary phases mixed in a ration of 7:3, with the upper layer of the solvent mixture being used as the DCCC mobile phase. Once the solute was loaded in a 10 ml sample chamber, elution commenced with the mobile phase passing through the stationary phase in an ascending manner. Fractions (120 drops per fraction) were collected at a rate of about 5 ml per hour on a Buchler Fractomette Alpha 200 automatic fraction collector, immediately on elution of the mobile phase. Separation was carried out at ambient temperature. Fractions 55-92 were shown by thin layer chromatography to contain TPA, and were combined to afford a residue (180 mg; 40% w/w of the sample submitted to DCCC.

Reverse-phase column chromatography. Further purification of the TPA in fractions 55-92 was achieved by the utilization of liquid column chromatography. The stationary phase was octylsilyl phase-bonded silica gel, which was eluted with mixtures of water-acetonitrile-methanol of decreasing polarity. Chromatography was effected under low pressure, using a Milton Roy Mini-Pump (Milton Roy Company, Laboratory Control Division, Riviera Beach, Florida). Fractions were collected on the automatic fraction collector described above, with each fraction representing 70 drops. Elution commenced with the solvent mixture water-acetonitrile-methanol in proportions by volume of 1:1:5 for fractions 1-35; in proportions by volume of 1:1:7 for fractions 36-70; and, in proportions by volume of 1:1:9 for fractions 71-130. Fractions 52 through 71 were shown by thin-layer chromatography to contain TPA, and were combined to afford a resin in 108 mg yield (60% w/w of the sample submitted to liquid column chromatography.

Preparative thin-layer chromatography. Final purification of TPA was achieved by preparative thin-layer chromatography of fractions 52-71 from the column chromatographic separation. The solute was applied to four silica gel G plates and developed once their full length in chloroform-ethyl acetate (9:11). Bands with the $R_f$ range 0.44–0.58 were visualized under short-wave UV light (254 nm), scraped from the plates, combined, and eluted with diethylether-methanol (1:1), using Pasteur pipettes plugged with cotton wool. A total of 29.3 mg of TPA was obtained in pure form at the conclusion of this step (yield of 0.22% of the starting croton oil used). Therefore, if scaled up and repeated, altogether 220 mg of TPA is obtainable per 100 g portion of croton oil. The TPA is of exceptionally high purity, being free of both polar and non-polar contaminants as shown by thin-layer chromatography, and being free of its phorbol 12,13-diester analogs as shown by electron-impact mass spectrometry.

EXAMPLE 2

Isolation of phorbol isomers. The hexane-soluble fraction (96.6 g) from the croton oil used in Example 1 from which TPA had been extracted was mechanically shaken for 14 hours after mixing with methanol (150 ml) saturated with $Ba(OH)_2.8H_2O$ (3.5 g). The hydrolysis was carried out under an atmosphere of nitrogen with the reaction vessel protected from light. Methanol was removed under reduced pressure below 40° C. Crude phorbol isomers were extracted with 8×100 ml acetone aliquots, filtered, and on reduction to dryness, 92.2 g of an acetone extract were obtained. The final acetone wash gave only a faint colorimetric test for the presence of phorbol. The acetone extract was dissolved in hexane (100 ml) and extracted with 3×50 ml methanol-water (10:1). Examination of the hexane layer by thin-layer chromatography, using ethylacetate-methanol (10:1) as solvent and silica gel G precoated plates, showed that no phorbol ($R_f$0.28) was present. Solvent was removed from the aqueous methanolic layer to yield 3.9 g of solid residue.

Purification of phorbol and 4α-phorbol. A portion (1.01 g) of the solid rsidue was submitted to DCCC using hexane-diethylether-n-propanol-ethanol-water (4:8:3:5:4) as solvent. The lower equilibrated phase was used as the mobile phase, and the sample was injected in a 1:1 mixture of the upper and lower phases, using a 10 ml sample chamber. Fractions of about 1 ml were collected at a rate of about 5 ml/hr on a Buchler Fractomette Alpha 200 automatic fraction collector, and were weighed on removal of solvent. DCCC using the above procedure was repeated for phorbol (23 mg) and the absorbance at 253 nm was measured for each fraction eluted. A void volume, representing passage of the mobile phase from the beginning of the separation until the elution of the first drop of mobile phase, was calculated as 27 ml.

Final purification of phorbol and 4α-phorbol was achieved by liquid column chromatography of the fractions in tubes 65-125 (45 mg), using octylsilyl-bonded silica gel, eluted with methanol-acetonitrile-water (1:1:6) at a flow rate of 29 ml/min. Phorbol and 4α- phorbol were eluted 10–20 ml and 24–27 ml respectively after injection.

Characterization of phorbol and 4α-phorbol. White needles of phorbol-ethyl acetate solvate (8.9 mg; 0.34% w/w; m.p. 230° C.) were obtained after crystallization from ethyl acetate, which exhibited identical thin-layer chromatography and mass spectral characteristics to an authentic sample of the compound.

4α-Phorbol (6.1 mg; 0.23% w/w) was characterized by comparison of its PMR and mass spectra with published data.

Heretofore, the DCCC procedure has been applied primarily to the separation of naturally-occurring compounds of relatively high polarity. The herein disclosed procedure makes it possible to isolate and purify naturally-occurring, non-polar compounds, which procedure utilizes DCCC and a unique solvent system to effect the desired separation and purification. In particular, the procedure provides a rapid and reliable method for the isolation of TPA, phorbol, and 4α-phorbol in very high purity.

Although this invention has been described with reference to certain preferred embodiments thereof, it is understood that variations and modifications can be effected within the spirit and scope of the appended claims. It is intended that all material contained in the above description and examples shall be interpreted in an illustrative and not in a limiting sense.

What is claimed is:

1. A method for isolating 12-O-tetradecanoylphorbol-13-acetate(TPA) in high purity from croton oil comprising the steps of
    (a) extracting the croton oil with an aqueous alcohol solution to obtain a crude TPA extract;
    (b) purifying the crude TPA extract by droplet counter-current chromatography(DCCC) wherein the mobile and stationary phases are derived from an equilibrated mixture of hexane-diethylether-n-propanol-ethanol-water, the separated upper layer of which comprises the stationary phase and the bottom layer of which the mobile phase, and the composition of which mixture is such that the distribution coefficient for TPA, as defined by the ration of its concentration in the stationary phase divided by that in the mobile phase, lies in the range of from about 3.0 to about 12.0; and
    (c) further purifying the TPA by liquid-column chromatography followed by thin-layer chromatography.

2. The method of claim 1 wherein the aqueous alcohol solution comprises aqueous methanol, and where the crude TPA is dissolved in a mixture of the stationary and mobile phases to comprise the feed solution for DCCC.

3. The method of claim 1 wherein the equilibrated mixture comprises hexane-diethylether-n-propanol-ethanol-water in proportions by volume of about 1:2:1:1:1 to provide a distribution coefficient for TPA in the range of from about 5.0 to about 8.0.

4. The method of claim 1 wherein said liquid column chromatography utilizes octylsilyl phase-bonded silica gel as the stationary phase and eluting is effected with mixtures of water-acetonitrile-methanol of decreasing polarity.

5. The method of claim 4 wherein said thin-layer chromatography utilizes silica gel plates developed with chloroform-ethylacetate solvent.

6. A method for isolating the isomers of phorbol in high purity from croton oil comprising the steps of:
    (a) extracting the croton oil with an aqueous alcohol solution to remove a crude TPA extract;
    (b) hydrolyzing the residual phorbol esters in the extracted croton oil with a base under an inert atmosphere to provide a crude phorbol hydrolyzate;
    (c) purifying and separating the hydrolyzate into phorbol and 4α-phorbol by droplet counter-current chromatography (DCCC) wherein the mobile and stationary phases are derived from an equilibrated mixture of hexane-diethylether-n-propanol-ethanol-water, the separated upper layer of which comprises the stationary phase and the bottom layer of which the mobile phase, and the composition of which mixture is such that the distribution coefficient for the phorbol isomers, as defined by the ratio of their concentrations in the stationary phase divided by that in the mobile phase, lies in the range of from about 3.0 to about 12.0; and
    (d) further purifying the phorbol isomers by liquid column chromatography.

7. The method of claim 6 wherein the aqueous alcohol solution comprises aqueous methanol and wherein the hydrolysis is effected with methanol saturated with $Ba(OH)_2 \cdot 8H_2O$ under an inert atmosphere.

8. The method of claim 6 wherein the equilibrated mixture comprises hexane-diethylether-n-propanol-ethanol-water in proportions by volume of about 1:2:1:1:1 to provide a distribution coefficient for the phorbol isomers in the range of from about 5.0 to about 8.0.

9. The method of claim 8 wherein said liquid column chromatography utilizes octylsilyl phase bonded silica gel as the stationary phase and eluting the isomers is effected with mixtures of water-acetonitrile-methanol of decreasing polarity.

* * * * *